(12) United States Patent
Samuelsson et al.

(10) Patent No.: US 11,234,650 B2
(45) Date of Patent: Feb. 1, 2022

(54) MEASUREMENT SYSTEM

(71) Applicant: ST. JUDE MEDICAL COORDINATION CENTER BVBA, Zaventem (BE)

(72) Inventors: Magnus Samuelsson, Uppsala (SE); Sauli Tulkki, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 0 days.

(21) Appl. No.: 16/930,540

(22) Filed: Jul. 16, 2020

(65) Prior Publication Data

US 2020/0345306 A1 Nov. 5, 2020

Related U.S. Application Data

(60) Continuation of application No. 16/401,156, filed on May 2, 2019, now Pat. No. 10,736,573, which is a (Continued)

(51) Int. Cl.
*A61B 5/00* (2006.01)
(52) U.S. Cl.
CPC .............. *A61B 5/6852* (2013.01); *A61B 5/00* (2013.01); *A61B 5/6851* (2013.01)
(58) Field of Classification Search
CPC .... A61B 1/00; A61B 5/00; A61B 5/02; A61B 5/03; A61B 5/04; A61B 5/6801;
(Continued)

(56) References Cited

U.S. PATENT DOCUMENTS

| 4,785,822 A | 11/1988 | Wallace |
| 5,184,619 A * | 2/1993 | Austin ................ A61B 5/035 |
| | | 600/376 |

(Continued)

FOREIGN PATENT DOCUMENTS

| CN | 1168625 A | 12/1997 |
| CN | 1625742 A | 6/2005 |

(Continued)

OTHER PUBLICATIONS

Extended European Search Report, Application No. 20182598.1, dated Oct. 15, 2020, 6 pages.

(Continued)

*Primary Examiner* — Van T Trieu
(74) *Attorney, Agent, or Firm* — Foley & Lardner LLP

(57) ABSTRACT

A blood pressure measurement system comprising a pressure sensor guide wire comprising a pressure sensor located in a distal region of the pressure sensor guide wire that is configured to be inserted into a blood vessel of a human body and a transceiver unit communicatively coupled to the pressure sensor guide wire. The transceiver unit comprises a housing adapted to be used external to the human body, a sensor signal adapting circuitry configured to process pressure sensor values generated by the pressure sensor to create processed pressure sensor values, and a first transceiver configured to wirelessly transmit a signal representing the processed pressure sensor values using first, second, and third packets at first, second, and third frequencies.

20 Claims, 8 Drawing Sheets

PATIENT

PRESSURE SENSOR WIRE   TRANSCEIVER UNIT   WIRELESS LINK   COMMUNICATION UNIT   EXTERNAL DEVICE

Related U.S. Application Data continuation of application No. 15/865,519, filed on Jan. 9, 2018, now Pat. No. 10,314,488, which is a continuation of application No. 15/415,271, filed on Jan. 25, 2017, now Pat. No. 9,888,848, which is a division of application No. 14/950,847, filed on Nov. 24, 2015, now Pat. No. 9,585,566, which is a continuation of application No. 14/218,017, filed on Mar. 18, 2014, now Pat. No. 9,220,461, which is a division of application No. 13/847,226, filed on Mar. 19, 2013, now Pat. No. 8,698,638, which is a continuation of application No. 13/444,487, filed on Apr. 11, 2012, now Pat. No. 8,410,940, which is a continuation of application No. 12/771,167, filed on Apr. 30, 2010, now Pat. No. 8,174,395, which is a continuation-in-part of application No. 11/601,853, filed on Nov. 20, 2006, now Pat. No. 7,724,148.

(58) Field of Classification Search
CPC ... A61B 5/6846; A61B 5/6848; A61B 5/6851; A61B 5/6852; A61B 5/6862; H04B 1/713; H04B 1/7143; H04B 1/7163
See application file for complete search history.

(56) References Cited

U.S. PATENT DOCUMENTS

| | | |
|---|---|---|
| 5,312,446 A | 5/1994 | Holschbach et al. |
| 5,387,194 A | 2/1995 | Williams et al. |
| 5,484,404 A | 1/1996 | Schulman et al. |
| 5,568,815 A | 10/1996 | Raynes et al. |
| 5,769,843 A | 6/1998 | Abela et al. |
| 5,807,253 A | 9/1998 | Dumoulin et al. |
| 5,899,860 A | 5/1999 | Pfeiffer et al. |
| 5,919,221 A | 7/1999 | Miesel |
| 6,167,763 B1 | 1/2001 | Tenerz et al. |
| 6,233,476 B1 | 5/2001 | Strommer et al. |
| 6,248,080 B1 | 6/2001 | Miesel et al. |
| 6,264,611 B1 | 7/2001 | Ishikawa et al. |
| 6,292,697 B1 | 9/2001 | Roberts |
| 6,312,380 B1 | 11/2001 | Hoek et al. |
| 6,391,005 B1 | 5/2002 | Lum et al. |
| 6,428,336 B1 | 8/2002 | Akerfeldt |
| 6,547,757 B1 | 4/2003 | Kranz et al. |
| 6,565,514 B2 | 5/2003 | Svanerudh et al. |
| 6,615,067 B2 | 9/2003 | Hoek et al. |
| 6,754,608 B2 | 6/2004 | Svanerudh et al. |
| 6,970,742 B2 | 11/2005 | Mann et al. |
| 6,996,431 B2 | 2/2006 | Ben-Haim et al. |
| 7,317,409 B2 | 1/2008 | Conero |
| 7,326,088 B2 | 2/2008 | Tulkki |
| 7,328,070 B2 | 2/2008 | Gerber et al. |
| 7,610,093 B2 | 10/2009 | Gerber et al. |
| 7,623,923 B2 | 11/2009 | Gerber et al. |
| 7,724,148 B2 | 5/2010 | Samuelsson et al. |
| 7,946,997 B2 | 5/2011 | Hubinette |
| 8,174,395 B2 | 5/2012 | Samuelsson et al. |
| 8,216,151 B2 | 7/2012 | Smith |
| 8,410,940 B2 | 4/2013 | Samuelsson et al. |
| 8,698,638 B2 | 4/2014 | Samuelsson et al. |
| 8,948,836 B2 | 2/2015 | Reghabi et al. |
| 9,220,461 B2 | 12/2015 | Samuelsson et al. |
| 2002/0059827 A1 | 5/2002 | Smith |
| 2002/0165448 A1 | 11/2002 | Ben-Haim et al. |
| 2003/0141916 A1 | 7/2003 | Conero |
| 2003/0225318 A1 | 12/2003 | Montegrande et al. |
| 2004/0097804 A1 | 5/2004 | Sobe |
| 2005/0197585 A1 | 9/2005 | Brockway et al. |
| 2005/0268724 A1 | 12/2005 | Tenerz |
| 2006/0009817 A1 | 1/2006 | Tulkki |
| 2006/0116571 A1 | 6/2006 | Maschke et al. |
| 2007/0208252 A1 | 9/2007 | Makower |
| 2007/0255145 A1 | 11/2007 | Smith et al. |
| 2008/0119758 A1 | 5/2008 | Samuelsson et al. |
| 2009/0082678 A1* | 3/2009 | Smith ............... A61B 5/6851 600/486 |
| 2009/0124880 A1 | 5/2009 | Smith |
| 2010/0286536 A1 | 11/2010 | Samuelsson et al. |

FOREIGN PATENT DOCUMENTS

| | | |
|---|---|---|
| CN | 101396263 A | 4/2009 |
| EP | 1 774 905 A1 | 4/2007 |
| EP | 1 922 988 A1 | 5/2008 |
| JP | 62-082939 A | 4/1987 |
| JP | 06-055204 B | 7/1994 |
| JP | H10-505269 A | 5/1998 |
| JP | 11-230705 A | 8/1999 |
| JP | 2000-504249 A | 4/2000 |
| JP | 2001-509038 A | 7/2001 |
| JP | 2001-516271 A | 9/2001 |
| JP | 2005-237964 A | 9/2005 |
| JP | 2006-026406 A | 2/2006 |
| JP | 2006-511271 A | 4/2006 |
| JP | 2006-150082 A | 6/2006 |
| JP | 2007-105459 A | 4/2007 |
| JP | 2007-516782 A | 6/2007 |
| JP | 2008-514308 A | 5/2008 |
| JP | 2008-126086 A | 6/2008 |
| JP | 2008-532587 A | 8/2008 |
| JP | 2008-546362 A | 12/2008 |
| JP | 2010-502273 A | 1/2010 |
| JP | 2010-051801 A | 3/2010 |
| JP | 2010-148964 A | 7/2010 |
| WO | WO-93/09837 A1 | 5/1993 |
| WO | WO-96/05768 A1 | 2/1996 |
| WO | WO-97/27802 A1 | 8/1997 |
| WO | WO-99/37208 A1 | 7/1999 |
| WO | WO-03/075744 A2 | 9/2003 |
| WO | WO-2006/037082 A2 | 4/2006 |
| WO | WO-2006/133851 A2 | 12/2006 |
| WO | WO-2008/100208 A1 | 8/2008 |

OTHER PUBLICATIONS

Canadian Office Action, dated Jun. 26, 2015, 5 pages.
Chinese Office Action, Application No. 201710196000.7, dated Jul. 18, 2019, 5 pages.
Chinese Office Action, dated Jul. 27, 2015, 18 pages.
Chinese Office Action, dated Apr. 21, 2014, 18 pages.
European Application, Summons to Attend Oral Proceedings, Application No. 11718334.3, Sep. 29, 2015, 6 pages.
Extended European Search Report dated Aug. 18, 2016, 8 pages.
Extended European Search Report, EP 19163712.3, dated Jul. 8, 2019, 6 pages.
International Preliminary Report on Patentability, PCT/EP2011/056704, dated Nov. 6, 2012, 10 pages.
Japanese Office Action and English translation, Application No. 2016-097179, dated Jan. 30, 2018, 4 pages.
Japanese Office Action and English translation, Application No. 2018-102423, dated Jun. 11, 2019, 5 pages.
Japanese Office Action, dated Apr. 28, 2015, 8 pages.
Japanese Office Action, dated May 16, 2017, 4 pages.
USPTO Office Action, Office Action, U.S. Appl. No. 12/771,186, dated Oct. 3, 2012, 14 pages.
William F. Fearon et al., Novel Index for Invasively Assessing the Coronary Microcirculation, Circulation, Journal of the American Heart Association, 2003, pp. 107:3129-3132
U.S. Appl. No. 11/601,853, filed Nov. 20, 2006.
U.S. Appl. No. 12/771,167, filed Apr. 30, 2010.
U.S. Appl. No. 13/444,487, filed Apr. 11, 2012.
U.S. Appl. No. 13/847,226, filed Mar. 19, 2013.
U.S. Appl. No. 14/218,017, filed Mar. 18, 2014.
U.S. Appl. No. 14/950,847, filed Nov. 24, 2015.
U.S. Appl. No. 15/415,271, filed Jan. 25, 2017.
U.S. Appl. No. 15/865,519, filed Jan. 9, 2018.
"Search Report by Registered Search Organization," Application No. 2018-102423 and English translation, dated Apr. 2, 2019, 20 pages.

(56) References Cited

OTHER PUBLICATIONS

"Search Report by Registered Search Organization," Application No. 2013-506655 and English translation, dated Aug. 12, 2014, 65 pages.
"Search Report by Registered Search Organization," Application No. 2016-097179 and English translation, dated Mar. 24, 2017, 38 pages.
Japanese Office Action, Application No. 2018-102423, dated Jun. 11, 2019, 5 pages with English language translation.
Japanese Office Action, Application 2013-506655, dated Oct. 14, 2014, 4 pages with English language translation.
Japanese Office Action, Application 2016-097179, dated May 16, 2017, 4 pages with English language translation.

* cited by examiner

MEASUREMENT SYSTEM

CROSS-REFERENCE TO RELATED PATENT APPLICATIONS

The present application is a continuation of U.S. application Ser. No. 16/401,156, filed May 2, 2019, now U.S. Pat. No. 10,736,573, which is a continuation of U.S. application Ser. No. 15/865,519, filed on Jan. 9, 2018, now U.S. Pat. No. 10,314,488, which is a continuation of U.S. application Ser. No. 15/415,271, filed Jan. 25, 2017, now U.S. Pat. No. 9,888,848, which is a divisional of U.S. application Ser. No. 14/950,847, filed Nov. 24, 2015, now U.S. Pat. No. 9,585,566, which is a continuation of U.S. application Ser. No. 14/218,017, filed Mar. 18, 2014, now U.S. Pat. No. 9,220,461 which is a divisional of U.S. application Ser. No. 13/847,226, filed Mar. 19, 2013, now U.S. Pat. No. 8,698,638, which is a continuation of U.S. application Ser. No. 13/444,487, filed Apr. 11, 2012, now U.S. Pat. No. 8,410,940, which is a continuation of U.S. application Ser. No. 12/771,167, filed Apr. 30, 2010, now U.S. Pat. No. 8,174,395, which is a continuation-in-part of U.S. application Ser. No. 11/601,853, filed Nov. 20, 2006, now U.S. Pat. No. 7,724,148, the disclosures of which are incorporated by reference herein in their entirety.

FIELD OF THE INVENTION

The present invention relates to a transceiver unit and a communication unit for a pressure measurement system for measuring a physiological variable in a body.

BACKGROUND

In many medical procedures, medical personnel need to monitor various physiological conditions that are present within a body cavity of a patient. These physiological conditions are typically physical in nature—such as pressure, temperature, rate-of-fluid flow—and provide the physician or medical technician with critical information as to the status of a patient's condition. Obviously, the manner by which these types of parameters are measured and monitored must be safe, accurate and reliable.

One device that is widely used to monitor such conditions is the blood pressure transducer. A blood pressure transducer senses the magnitude of a patient's blood pressure, and converts it into a representative electrical signal. This electrical signal is then supplied to a vital signs monitor that displays, records or otherwise monitors the magnitude of the patient's blood pressure.

Traditionally, a blood pressure transducer has consisted of a pressure responsive diaphragm that is mechanically coupled to piezoresistive elements connected in a Wheatstone Bridge-type circuit arrangement. When the diaphragm is placed in fluid communication with a body cavity (such as within the arterial or venous system), pressure induced deflections of the diaphragm cause the resistive elements to be stretched (or compressed, depending on their orientation). According to well-known principles, this alters the resistance of the elements in a manner that is proportional to the applied pressure. The magnitude of the applied pressure can thus be detected by applying an excitation power signal (usually in the form of a voltage) to the inputs of the Wheatstone bridge circuit, and by simultaneously monitoring the bridge output signal. The magnitude of that signal reflects the amount by which the bridge resistance has changed, according to Ohm's law.

Typically, an electrical cable connects the Wheatstone bridge portion of the transducer sensor to a transducer amplifier circuit contained within the vital signs monitor. This amplifier circuit supplies the excitation power signal to the Wheatstone bridge, and simultaneously monitors the bridge output signal. The excitation power signal is typically in the form of a voltage and, depending on the monitor type and manufacturer, can have varying magnitudes and formats, both time-varying (sinusoidal, square-waved and pulsed) and time independent (DC).

According to the principles under which conventional Wheatstone bridge transducers operate, transducer amplifier circuits in most patient monitors have been designed to expect a sensor output signal having a magnitude that is proportional to the magnitude of the excitation power signal and also proportional to the magnitude of the sensed pressure. Because different monitors supply excitation power signals having different magnitudes and/or frequencies, standard proportionality constants have been developed. These proportionality standards allow any sensor to be readily adapted for use with any patient monitor also calibrated to adhere to the proportionality standard.

Several benefits are provided by this compatibility. Blood pressure transducers could be used interchangeably with patient monitors from different manufacturers. As such, medical personnel were not required to select a specific transducer for use with a specific monitor. Further, hospital investments in pre-existing patient monitors were preserved, thereby reducing costs. As a consequence, vital signs monitors adhering to these proportionality standards have achieved almost universal acceptance in medical environments.

However, the blood pressure transducers and monitors that have been previously used, and the resulting standards that have evolved, are not without drawbacks. For instance, the sensors used in these systems were typically positioned external to the patient's body and placed in fluid communication with the body cavity via a fluid-filled catheter line. Pressure variations within the body cavity are then indirectly communicated to the diaphragm by way of fluid contained with the catheter line. As such, the accuracy of such systems has suffered due to variations in hydrostatic pressure and other inconsistencies associated with the fluid column.

In response to this problem, miniaturized sensors using advanced semiconductor technologies have been developed. These types of transducer sensors are extremely accurate, inexpensive and still utilize the well known Wheatstone bridge-type of circuit arrangement, which typically, at least partly, is fabricated directly on a silicone diaphragm. Further, the sensors are sufficiently small such that they can actually be placed on the tip of an insertable guide wire and reside directly within the arteries, tissues or organs of the patient. This eliminates the need for a fluid line because the fluid pressure is communicated directly to the transducer diaphragm. As a result, these sensors—often referred to as guide wire-tipped transducers—provide a much more accurate measurement of the patient's blood pressure.

Unfortunately, the electrical configurations of these miniaturized semiconductor sensors are not always compatible with the transducer amplifiers in existing patient monitors. For instance, the miniaturized sensors often cannot operate over the entire range of excitation signal magnitudes and frequencies found among the various types of patient monitors. Thus, they cannot be connected directly to many of the patient monitors already in use. To be used with such existing monitors, a specialized interface must be placed between the sensor and the monitor. Such an arrangement necessitates additional circuitry on the interface and, because existing monitors have been designed to provide only limited amounts of power, the additional circuitry may require an independent source of electrical power. As a consequence, use of the newer miniaturized sensors often adds cost and complexity to the overall system.

In addition, because of the above limitations, these sensors must often be configured to generate an output signal which is proportional to the pressure sensed, but that is not related to the excitation signal, supplied to the sensor by the monitor, in a way that is directly usable by the physiology monitor, e.g. the sensitivity may be different. As discussed, this does not conform with the electrical format required by the many monitors that are commercially available and already in widespread use. As such, the newer sensors can only be used with specific monitor types, thereby requiring additional, and often redundant, equipment to be purchased. This is especially undesirable given the cost sensitivities so prevalent in today's health care environment.

The Association for the Advancement of Medical Instrumentation ("AAMI") has defined power requirements for physiology monitors and in particular the input/output connector to a sensor wire assembly must comply with the standard set by American National Standards Institute ("ANSI")/AAMI BP22-1994 (referred to as "BP22" in the following).

According to the BP22-standard an input/output connector arranged at the proximal end of a five line connector cable includes a pair of differential output signal lines. The output signal lines are driven by a sensor adapting circuitry's output digital to analog converters (discussed further herein below). The differential output signal, by way of example, operates at 5 $\mu V/mmHg/V_{EXC}$. An operation range of $-150$ $\mu V/V$ to $1650$ $\mu V/V$ therefore represents a sensed pressure range of $-30$ to $330$ mmHg. An exemplary resolution (minimum step) for the differential output signal is $0.2$ mmHg.

U.S. Pat. No. 5,568,815 discloses an interface circuit for interfacing a sensor to a patient monitor. The interface circuit includes a power supply circuit that receives an excitation power signal generated by the patient monitor, and derives therefrom unregulated and regulated supply voltages for use by the electrical components on the interface circuit. Further, the power supply circuit generates an appropriate sensor excitation signal. The interface circuit further includes receiving circuitry for receiving a sensor output signal generated by the sensor. A scaling circuit then scales that signal into a parameter signal that is proportional to the physiological condition detected by the sensor, and that is also proportional to the excitation power signal generated by the patient monitor.

An obvious drawback of the device of U.S. Pat. No. 5,568,815 is that, in order to connect the sensor to the monitor, a separate additional unit in the form of the interface circuit is required.

Furthermore, in U.S. Pat. No. 5,568,815 is also discussed the issues of having an electrically conducted device such as a pressure transducer connected both to a patient and to an electronic monitoring instrument. Great care must then be taken to insure that electrical currents at standard power line frequencies cannot flow from the patient, through the transducer connection, and to ground. An additional risk occurs in patents which are undergoing defibrillation while having an electrically conductive transducer attached.

Thus, the insulation problem has previously been addressed by using fiber-optics or opto-isolator devices to achieve the connection with the monitor device.

The physical connection between the sensor device and the monitor device must be seen in the total set-up during pressure measurements which also may include other instruments involved having its cables or connections which may result in a complex and non-user-friendly environment for the user. In this connection also the sterilisation issue must be mentioned; in the systems according to the prior art there are physical connections, irrespectively if it is for electrical or optical communication purposes, directly to the monitoring device, which require that the entire system must be sterilized and eventually disposed.

A solution to the insulation problem is to use wireless communication to transmit the measure values from the sensor to the monitoring device.

In U.S. Patent Application Publication No. 2006/0009817, assigned to the assignee of the present application, a system and a method for obtaining a wireless communication of physiological variables are disclosed. The system comprises a control unit providing a communication interface preferably for radio frequency communication using a carrier signal, which is generated by a monitoring device. The control unit is arranged with a modulator for modulating the carrier signal with a signal representing a measured physiological value received from a sensor disposed in the body. Thus, the function of the control unit is dependant upon the generation of a carrier signal from an external unit in order to be able to transfer the measured variables.

Furthermore, the above-mentioned U.S. Patent Application Publication only indicates that the control unit may be attached to the core wire of the guide wire via a connection wire using a suitable connector means, such as a crocodile clip-type connector, or if the connection wire is omitted, directly connecting the core wire to the control unit by a suitable connector. The connector is not further discussed in the above application.

Thus, in the complex environment of an operating room and taken the different drawbacks of the prior art solutions, the general object of the present invention is to achieve an improved device being more user-friendly and reliable than the presently available systems.

SUMMARY

The above-mentioned object is achieved by the present invention described herein.

In particular the present invention obviates the need of a physical connection between the patient and the monitoring device by arranging a reliable wireless link connection between a an easy-to-use transceiver unit and a communication unit, and in particular that the measured pressure data is generated by the transceiver unit and transferred as a data stream. The transceiver unit, when receiving pressure sensor data from the pressure sensor, is adapted to self-contained, directly or at a later time, generate a wireless transmission of pressure data to the communication unit without using any carrier wave from the communication unit or any other unit.

The communication unit is adapted to be connected to an external device by a standard input/output connector in accordance with an established standard or in accordance with relevant parts of an established standard, e.g. BP22 or USB, as briefly discussed in the background section.

BRIEF DESCRIPTION OF THE DRAWINGS

Preferred embodiments of the present invention will be described in detail in the following with reference made to accompanying drawings, in which.

DETAILED DESCRIPTION OF PREFERRED EMBODIMENTS OF THE INVENTION

In the prior art, it is known to mount a sensor on a guide wire and to position the sensor via the guide wire in a blood vessel in a living body to detect a physical parameter, such as pressure or temperature. The sensor includes elements that are directly or indirectly sensitive to the parameter. Numerous patents describing different types of sensors for measuring physiological parameters are owned by the applicant of the present patent application. For example, temperature could be measured by observing the resistance of a conductor having temperature sensitive resistance as described in U.S. Pat. No. 6,615,067. Another exemplifying sensor may be found in U.S. Pat. No. 6,167,763, in which blood flow exerts pressure on the sensor which delivers a signal representative of the exerted pressure.

In order to power the sensor and to communicate signals representing the measured physiological variable to an external physiology monitor, one or more cables or leads for transmitting the signals are connected to the sensor, and are routed along the guide wire to be passed out from the vessel to the external physiology monitor, conventionally via physical cables. In addition, the guide wire is typically provided with a central metal wire (core wire) serving as a support for the sensor and (optionally) also as an electrical connection to the sensor, and a surrounding tubing. Hence, a guide wire typically comprises a core wire, leads and a protective tubing.

Figure 1:
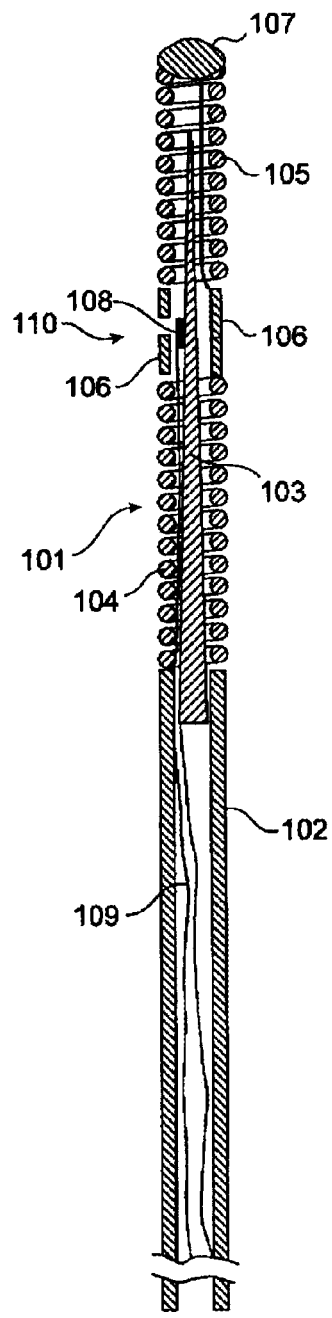
FIG. 1 shows an exemplifying sensor mounted on a guide wire in accordance with prior art and which is applicable herein.

FIG. 1 shows an exemplifying sensor mounted on a guide wire in accordance with conventional design which is applicable for the present invention. The sensor guide wire 101 comprises a hollow tube 102, a core wire 103, a first spiral portion 104, a second spiral portion 105, a jacket or sleeve 106, a dome-shaped tip 107, a sensor element or chip 108, and one or several electrical leads 109. The tube 102 has typically been treated to give the sensor guide construction a smooth outer surface with low friction. The proximal end of the first spiral portion 104 is attached to the distal end of the hollow tube 102, while the distal end of the first spiral portion 104 is attached to the proximal end of the jacket 106. The proximal end of the second spiral portion 105 is connected to the distal end of the jacket 106, and the dome-shaped tip 107 is attached to the distal end of the second spiral portion 105. The core wire 103 is at least partly disposed inside the hollow tube 102 such that the distal portion of the core wire 103 extends out of the hollow tube 102 and into the second spiral portion 105. The sensor element 108 is mounted on the core wire 103 at the position of the jacket 106, and is connected to an external physiology monitor (not shown in the FIG. 1) via the electrical leads 109. The sensor element 108 comprises a pressure sensitive device in the form of a membrane (not shown in the FIG. 1), which through an aperture 110 in the jacket 106 is in contact with a medium, such as blood, surrounding the distal portion of the sensor guide wire 101.

Figure 2:
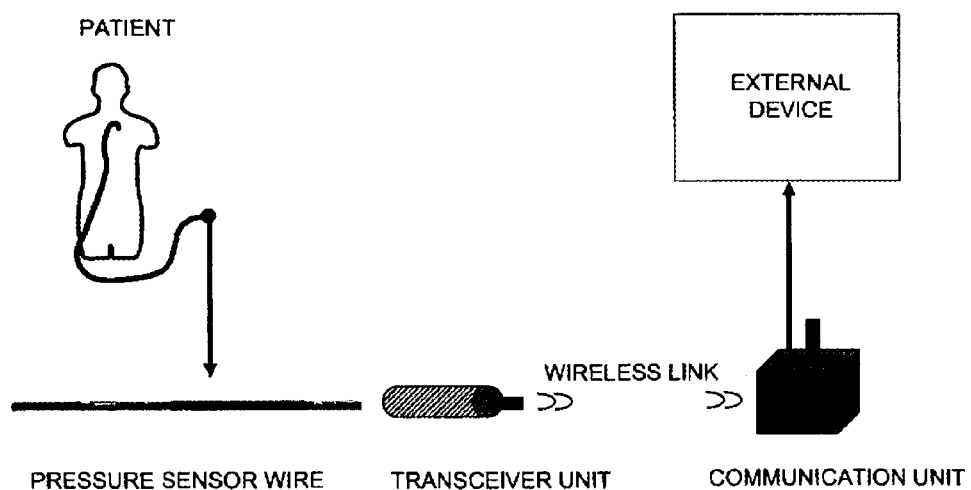
FIG. 2 schematically illustrates a measurement system according to the present invention.

FIG. 2 is a schematic overview illustrating the application of the present invention.

The pressure measurement system according to the present invention comprises a pressure sensor wire with a pressure sensor to measure pressure inside a patient, and to provide measured pressure data to an external device. The pressure sensor wire is adapted to be connected, at its proximal end, to a transceiver unit adapted to wirelessly communicate via a radio frequency signal with a communication unit arranged in connection with an external device (also referred to as external physiology monitor), in order to transfer measured pressure data to the external device.

The external device may be a dedicated device, i.e. a patient monitoring device, preferably provided with a monitor, or a PC (personal computer) provided with relevant software and external connections to receive and to process the measured data from the pressure measurement system. One example of a dedicated device applicable herein is disclosed in U.S. Pat. No. 6,565,514. A preferred embodiment of the present invention may have the external device be a standard cath lab monitor system; however, other external devices are contemplated, such as a mobile unit or a device where the data is sent directly to a mobile unit. Such mobile units may include, for example, a mobile phone, an iPhone, and a Blackberry with specific applications.

Figure 3:
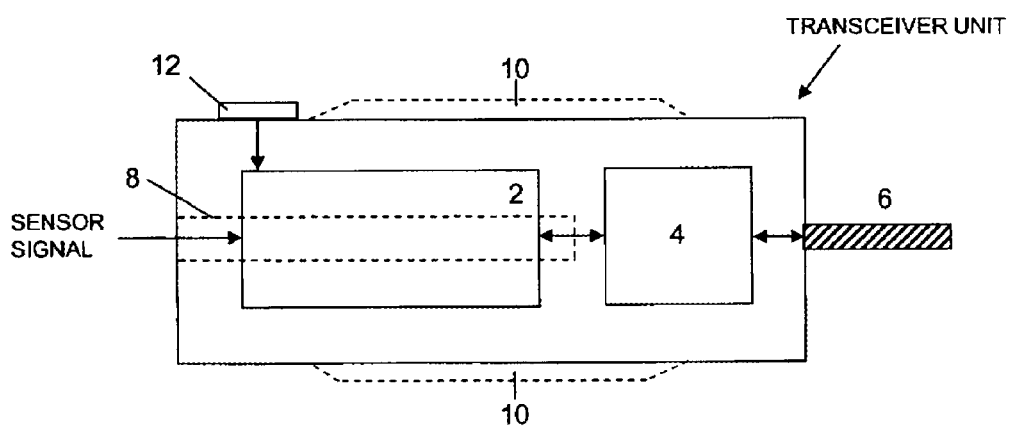
FIG. 3 shows a block diagram schematically illustrating a transceiver unit according to a preferred embodiment of the present invention.

FIG. 3 shows a block diagram schematically illustrating the transceiver unit according to the present invention. As shown in FIG. 1 the transceiver unit is adapted to be connected to the proximal end of a pressure sensor wire provided, at its distal end, with a pressure sensor to measure pressure inside a patient. Preferably, the transceiver unit comprises a sensor signal adapting circuitry 2, which will be described in greater detail below, a communication module 4, connected to the adapting circuitry 2, that will handled the wireless communication with the communication unit.

In particular during the specific situation where a number of transceiver units are arranged to communicate with one communication unit, also single-directional communication may be used, primarily for sake of obtaining a reliable communication link.

The measured pressure data is independently generated by the transceiver unit and transferred as a data stream to the communication unit at a prescribed frequency range (in the case where the communication signal is a radio frequency signal), to be further discussed below.

According to a preferred embodiment the communication signal is a radio frequency signal, and that embodiment will be described in detail below.

Furthermore, according to the preferred embodiment the radio frequency signal transmits the data as data packets, i.e. in a digital form. The radio frequency transmission may, as an alternative, be an analogue data transmission.

Generally the communication signal may be an electromagnetic wave signal, e.g. a radio frequency signal, an infrared signal, or a light signal.

According to alternative embodiments the communication signal may be any wirelessly transmitted signal, e.g. an ultrasound signal or a magnetic signal. A person skilled in the art may easily adapt the described system, i.e. the transceiver unit and communication unit, to use any of the mentioned communication signals.

The preferred embodiment where the communication signal is a radio frequency signal will now be described in detail. Although the transceiver unit and the communication unit are described in connection with the preferred embodiment it should be appreciated that relevant features would be equally applicable in case any of the alternative communication signals is used.

With references to FIGS. 2 and 3, the communication module is connected to an antenna 6. In the figures the antenna is illustrated as protruding outside the transceiver unit but may, as in an alternative, be integrated into the housing of the transceiver unit. The pressure sensor wire is adapted to be inserted into an elongated aperture 8 of the transceiver unit. The aperture is at its inner surface provided with a number of electrical connecting surfaces (not shown) to be connected to electrode surfaces at the proximal end of the pressure sensor wire when inserted into the aperture 8. The transceiver unit is further provided with wire fastening means (not shown) to firmly fixate the wire when correctly inserted into the aperture.

According to a preferred embodiment the transceiver unit is adapted to receive the proximal end to the pressure sensor wire having an outer diameter of 0.35 mm, i.e. the inner diameter of the elongated aperture 8 is slightly larger than 0.35 mm.

Figure 6:
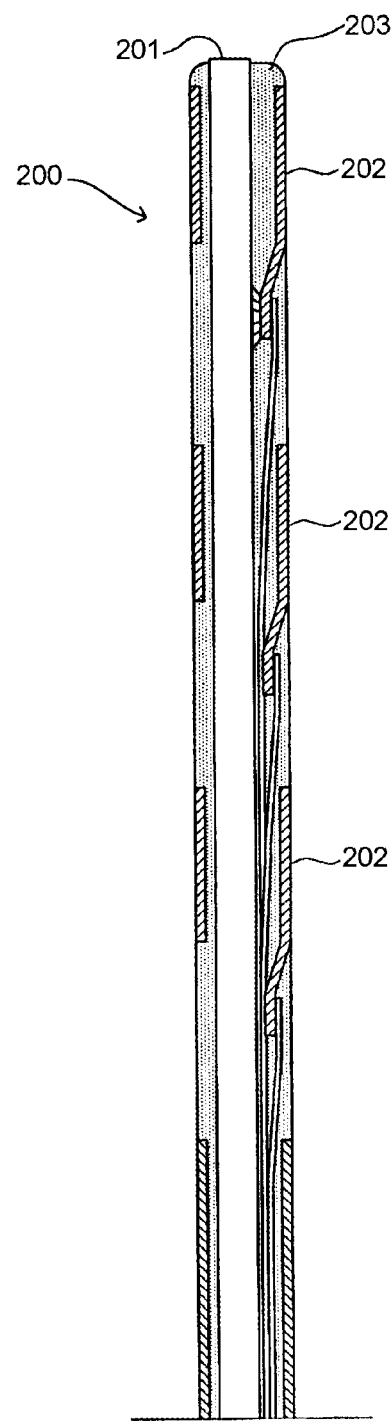
FIG. 6 schematically illustrates a male connector according to an embodiment of the present invention.

U.S. Pat. No. 5,938,624 relates to a male connector (shown in FIG. 6) with a continuous surface for a guide wire which preferably is applied as a male connector for the proximal end of the pressure sensor wire to be connected to a transceiver unit according to the present invention. The male connector 200 includes a core wire 201, and conductive members 202 spaced apart longitudinally along the core wire. A continuous insulating material 203 is disposed between the guide wire and the conductive members and the insulating material having an outer surface coextensive with outer surfaces of the conductive members.

Figure 7:
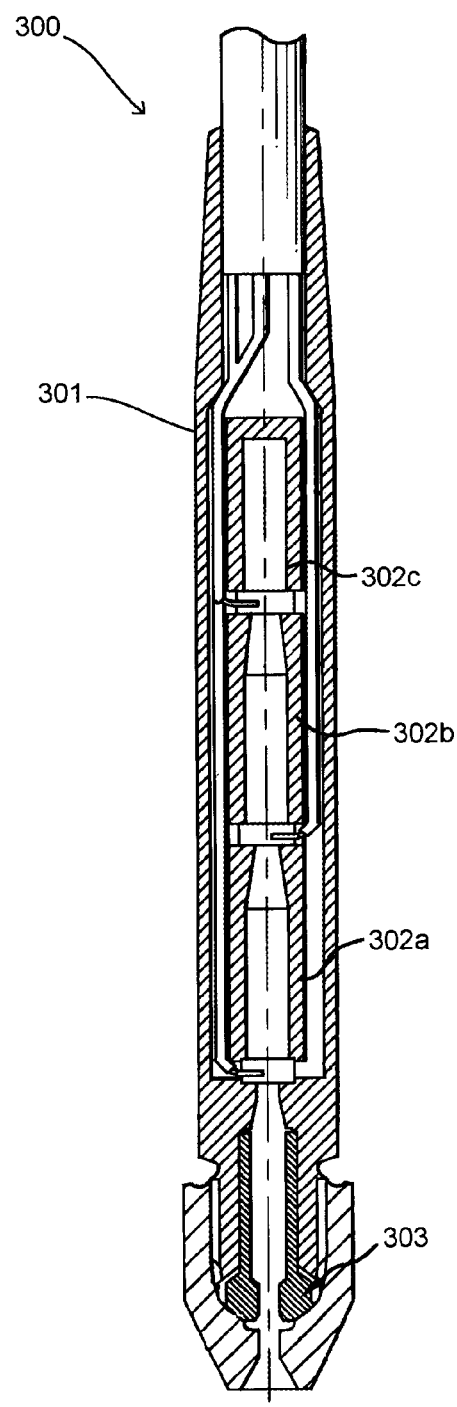
FIG. 7 schematically illustrates a female connector according to an embodiment of the present invention.

As mentioned above, the transceiver unit according to the present invention is provided with a fastening means to fasten the proximal end of the pressure wire to the transceiver unit. The fastening means may be a female connector of the type disclosed in U.S. Pat. No. 6,428,336 (shown in FIG. 7) into which a male connector of the kind described above may be inserted and secured to provide electrical contact with the contact surfaces of the male connector. The female connector 300 comprises an insulating hollow housing 301 containing three hollow contact members 302a, 302b, and 302c to make contact with the conductive members of the male connector. At the distal end of the female connector, the fastening means 303 for securing the male connector in the female connector is provided.

The male connector of the pressure sensor wire used in respect of the present invention is preferably compatible with the female connector disclosed in U.S. Pat. No. 6,428,336.

When the pressure sensor wire is fixated to the transceiver unit the unit may be used as a "handle" when guiding the pressure sensor wire during insertion into a patient. Preferably the transceiver unit is provided with guiding means 10, e.g. in the form of one or many elongated ribs on the outer surface of the transceiver unit, or by providing the transceiver unit with a roughened surface.

The pressure sensor wire may be fixated to the transceiver unit such that as the transceiver unit is rotated along its longitudinal axis the sensor wire is also rotated, which often is necessary in order to guide the sensor wire during the insertion procedure. As an alternative, the sensor wire is fixated to the transceiver unit in such way that the sensor wire may be rotated in relation to the transceiver unit. The rotation of the sensor wire is then achieved by firmly holding the transceiver unit by one hand and by rotating the sensor wire by the other hand.

The transceiver unit is preferably activated and initiated via an activation button 12 arranged at the housing of the unit. The activation button is preferably mechanically activated.

According to an alternative embodiment the transceiver unit is activated and initiated when the proximal end to the sensor wire is correctly inserted into the unit. This may e.g. be achieved by arranging a push button at the bottom of the cavity into which the pressure wire is inserted.

According to another alternative embodiment the transceiver unit is activated and initiated when electrical connections are established between corresponding electrical contact surfaces of the female and male connectors, respectively.

According to still another alternative embodiment the transceiver unit is activated and initiated by a remote signal generated from the communication unit in response of a command from the monitoring device.

The transceiver unit comprises energy means to energize the transceiver unit and the circuitry of the connected pressure sensor wire. The energy means is preferably a battery or a capacitor that e.g. may be included in the sensor signal adapting circuitry.

The pressure sensor wire as well as the transceiver unit are preferably disposable units that must be able to sterilise prior use.

According to an alternative embodiment of the invention, in order to further improve the user-friendliness of the transceiver unit, an attachment means is provided at the housing of the unit. The attachment means may be in the form of a strap, a clip or a hook, i.e. any mechanical attachment means enabling the transceiver unit to be stationary during use.

Figure 4:
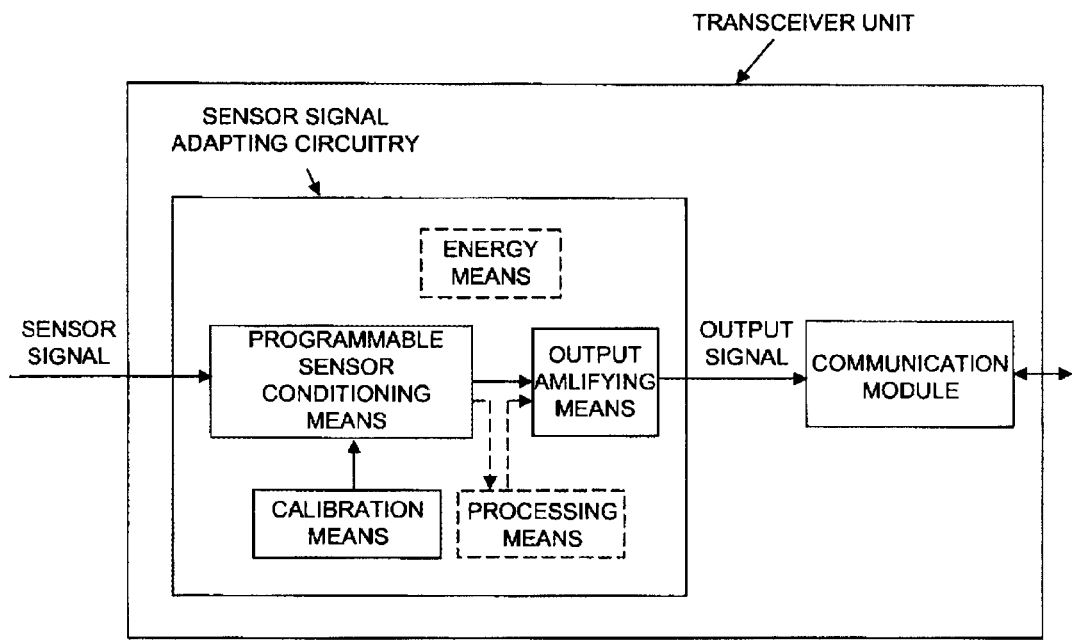
FIG. 4 shows a block diagram schematically illustrating a transceiver unit including a sensor signal adapting circuitry according a preferred embodiment of the present invention

FIG. 4 shows a block diagram schematically illustrating a sensor signal adapting circuitry applicable in the present invention and preferably integrated into the transceiver unit.

With references to FIGS. 1 and 2 the pressure sensor wire comprises a sensor element for measuring the physiological variable and to generate a sensor signal in response of said variable, a guide wire having said sensor element at its distal portion, preferably close to its distal end, and adapted to be inserted into the body in order to position the sensor element within the body. The transceiver unit comprises the sensor signal adapting circuitry (FIG. 4), wherein the sensor signal is applied to the adapting circuitry that is adapted to automatically generate an output signal, related to the sensor signal, in a format such that the measured physiological variable is retrievable by an external device. According to a preferred embodiment the sensor signal adapting circuitry comprises a programmable sensor conditioning means, a calibration means, being a storage means into which calibration data may be supplied, stored and altered, e.g. an electrically erasable programmable read-only memory (EEPROM), energy means and an output amplifying means.

The programmable sensor conditioning means is preferably a PGA309 programmable analog sensor conditioner (available from Texas Instruments Inc.) specifically designed for bridge sensors.

According to a preferred embodiment of the present invention the external device supplies the sensor signal adapting circuitry with a reference voltage value wirelessly via the radio link and the corresponding voltage is applied from the energy means in the transceiver unit. By considering the signal standard with which the external device complies, which is indicated to the adapting circuitry by means of the reference voltage, and the actual value of the physical parameter measured by the sensor element, the signal adapting circuitry will process the signal from the sensor element such that an adapted signal in accordance with the standard expected by the monitor may be wirelessly sent back to the external device.

The communication between the transceiver unit and the communication unit is preferably performed in a so-called license-free radio frequency interval.

The term "license-free radio" refers to the permission granted by government agencies to allow multiple radios to operate in a specified frequency band at one time. These license-free bands are known as the ISM (Industrial, Scientific and Medical) bands.

The two most commonly used ISM bands are referred to as the 900 MHz and the 2.4 GHz bands. Both permit the use of license-free Spread Spectrum radios within them. For the most part, the 900 MHz band is used in the Americas. The 2.4 GHz band is used (with differing power constraints) throughout most of the world. While there are some differences between the characteristics of the two bands, the 900 MHz band typically allows for higher power and longer distance transmissions while the 2.4 GHz band, with its wider bandwidth, allows for higher data rates. In Europe, the 869 MHz and 433 MHz bands are also classified as ISM bands and China has opened the 220 MHz band to license-free radios.

In an embodiment of the present invention a frequency band of 2.4 GHz (2.2-2.6 GHz) is used. A typical communication distance would be less than 10 meters.

In order to achieve a secure transmission of the sensor values from the transceiver unit to the communication unit, preferably a frequency hopping technique is used, e.g. by use of Bluetooth. The frequency hopping technique is well-known to persons skilled in the art of radio communication, and will therefore only briefly be described herein.

The transceiver unit comprises a first communication module to handle the radio frequency communication with the communication unit that is provided with a second communication module.

When the pressure sensor wire has been inserted into the transceiver unit and the communication unit is connected to the external device the system is ready for use.

By pressing the activation button on the transceiver unit it is activated and will then try to establish a radio link connection with the communication unit. This is preferably performed by a conventional handshake procedure in order to identify the transceiver unit. The system is now ready to receive measured sensor data.

Pressure sensor values measured at specific times, exemplary designated 1, 2, 3, 4, 5, etc., are respectively designated P1, P2, P3, P4, P5, etc, are applied to the communication module of the transceiver unit. These values are preferably transmitted in packets of three values per packet, e.g. P1, P2 and P3, forming packet P1P2P3; the next packet comprises values P2, P3 and P4 forming packet P2P3P4, and the next packet comprises values P3, P4 and P5 forming packet P3P4P5, etc. Consecutive packets are transmitted at different frequencies, i.e. packet P1P2P3 is sent at a first frequency F1, packet P2P3P4 is sent at a second frequency F2, and packet P3P4P5 is sent at a third frequency F3. Next packet would have been P4P5P6 and would have been sent at the first frequency F1, etc. This type of transmission is called a frequency hopping transmission. Thus, each pressure sensor value will then be sent three times, which increases the transmission security.

The packets received by the communication unit will then be unpacked by the second communication module in the communication unit and formatted such that the pressure values may be applied to the external device in accordance with the required signal standard, e.g. BP22 signal standard or USB standard, where they will be made available, e.g. on a display means.

As mentioned above the programmable sensor conditioner means is preferably implemented by means of a PGA309 programmable analog sensor conditioner. The PGA309 is particularly designed for resistive bridge sensor applications and contains three main gain blocks for scaling differential input bridge sensor signals. Hence, as discussed in the above, a signal representing the measured physiological variable may be adapted such that a signal in a format expected by the monitor is provided. This signal format is determined by the reference voltage supplied to the sensor signal adapting circuitry and the actual value of the signal measured by the sensor. The PGA309 can be configured for use with an internal or external voltage reference. According to the present invention, an internal reference voltage of e.g. +2.5V is supplied to the PGA309 from the energy means.

Thus, the conditioner means generates an analog output voltage signal related to the sensor signal such that the measured physiological variable, i.e. the pressure, may be retrieved by the external device.

Since each sensor element is an individual item with its own characteristics, each sensor assembly comprises a calibration means, preferably an electrically erasable programmable read-only memory (EEPROM) which contains individual calibration data obtained during calibration of the sensor element performed for each individual sensor wire assembly. The calibration is performed in connection with manufacture of the pressure sensor wire. Calibration data takes into account parameters such as voltage offsets and temperature drift, etc.

The bridge pressure sensor is preferably energized from the PGA309 via an excitation voltage $V_{EXC}$, generated by the PGA309 circuit. As an alternative the pressure sensor may be energized from a separate energy source, e.g. a battery or a capacitor means.

For a given excitation voltage $V_{EXC}$, e.g. generated by the PGA309 circuit, the output voltage ($V_{IN1}$-$V_{IN2}$) of the bridge is a voltage proportional to the pressure applied to the sensor. Hence, the sensor output voltage ($V_{IN1}$-$V_{IN2}$) (sensor signal in FIG. 4) of the bridge is proportional to the pressure applied to the sensor, which for a given pressure will vary with the applied excitation voltage. This sensor output voltage is preferably compensated for temperature variation at the site of the sensor and is applied to the PGA309 circuit. The PGA309 circuit also includes gain blocks for adjusting the output signal from that circuit and used in addition to the output amplifying means mentioned above.

According to another preferred embodiment a processing means, preferably a microprocessor (e.g. a PIC16C770 or a nRF24E1, shown with dashed lines in FIG. 4) may further be employed to process and adapt the analog output voltage $V_{OUT}$ of the conditioned sensor, which output voltage is supplied via the PGA309 programmable analog sensor conditioner. The analog output signal from the PGA309 circuit is A/D-converted prior it is applied to the processing means. To adapt the sensor signal to the BP22 signal standard, it may be necessary to process the sensor signal further before it is applied to the physiology monitor. For instance a multiplying digital-analog converter (DAC) which possibly is comprised in the processing means is supplied with digital data (e.g. a 12-bit word) representing the signal measured by the sensor element and the reference voltage. The resulting product is wirelessly sent (after having been filtered) to the external device and is proportional to the measured sensor signal and the reference voltage.

Figure 5:
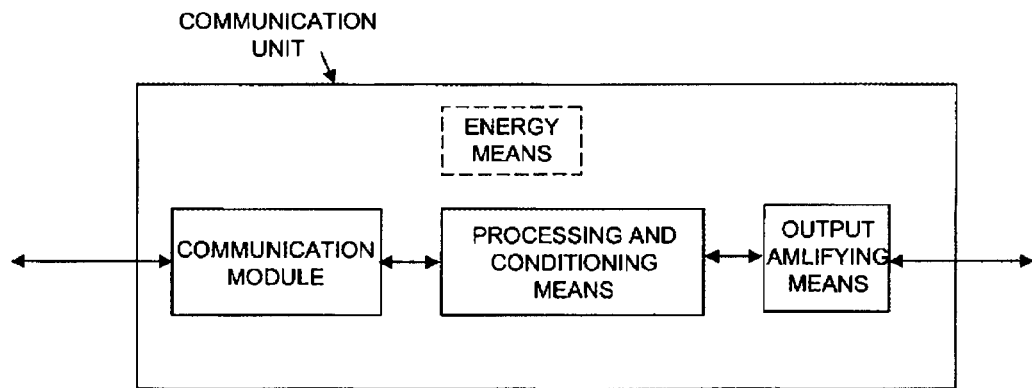
FIG. 5 shows a block diagram schematically illustrating a communication unit according to an alternative embodiment of the present invention.

In the preferred embodiment that has been described herein the adaptation of the sensor signal to the standard, e.g. BP22 signal standard, is performed in the transceiver unit, and in particular in the sensor signal adapting circuitry. However, this adaptation, in its entirety or only in parts, may, as an alternative, instead be performed by a corresponding circuitry arranged in the communication unit. This embodiment is schematically illustrated in FIG. 5. The wirelessly transmitted pressure sensor values would then be in the form of "raw" measured data that would be conditioned by a processing and conditioning means in the communication unit in order to be in a correct format to be supplied to the external system according to a prescribed standard format.

The above embodiment with respect to FIGS. 1-6 relates to the use of a pressure sensor wire comprising a pressure sensor element for measuring pressure inside the patient and generating a pressure sensor signal in pressure. Other types of sensors are also contemplated. For example, the sensor wire of FIG. 1 may include a sensor element configured to measure any physiological parameter, such as pressure inside the patient, temperature inside the patient, and blood flow inside the patient. For example, one suitable sensor may be a temperature sensor for measuring temperature by observing the resistance of a conductor having temperature sensitive resistance as described in U.S. Pat. No. 6,615,067, which is incorporate herein by reference in its entirety. Another suitable sensor may be a sensor for measuring blood flow as described in U.S. Pat. No. 6,167,763, which is incorporated by reference in its entirety, in which the blood flow can be measured either electrically or by using an ultrasonic technique. The electrical technique is based on temperature changes incurred by the velocity of flow, cooling being a function of flow rate. More rapid flow yields a larger temperature drop. Other suitable sensors may be found in U.S. Pat. Nos. RE 39,863 and 6,615,667, which are incorporated by reference in their entireties. Further suitable sensors may be blood analyte sensors for determine one or more chemical constituents in the blood, such as glucose, oxygenated or deoxygenated haemoglobin, or the like. The information transferred from the communication unit to the external device is then information related to the physiological parameter with the sensor values being sensor values related to the physiological parameter.

Additionally or alternatively, the sensor wire of FIG. 1 may include a sensor element configured to measure a non-physiological parameter. The non-physiological parameter may be a parameter inside or outside the body and be generated inside or outside the body. For example, the non-physiological parameter may be at least one of a magnetic field, a magnetic flux, an X-ray field, and/or an electromagnetic field near the body; an optical signal near the body; and/or the presence of an implantable, foreign and/or metallic device (such as a stent, needle, pacemaker, drug delivery device, or the like) inside the body. The information transferred from the communication unit to the external device is information related to the non-physiological parameter, and the sensor values are sensor values related to the non-physiological parameter.

Figure 8:
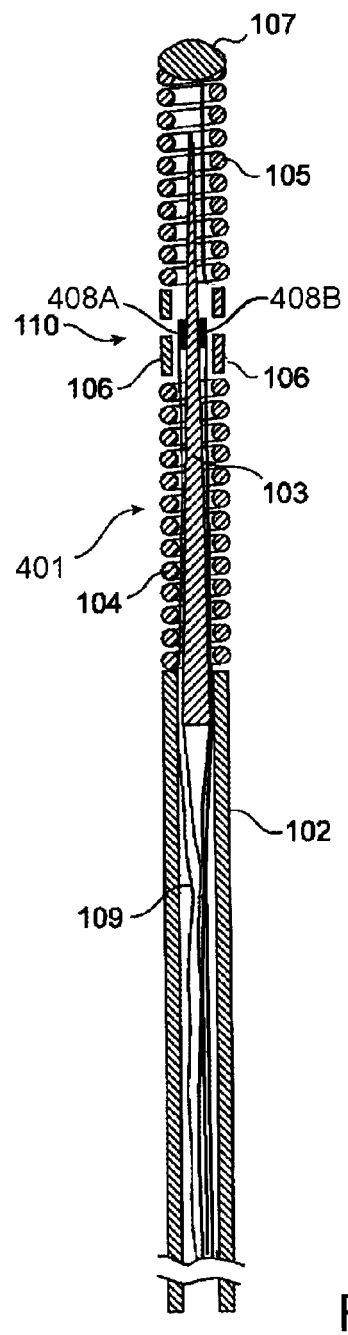
FIG. 8 schematically illustrates a measurement system according to another embodiment of the present invention.

With the detection of the non-physiological parameter, the sensor element can be used for positioning purposes, i.e. to establish the position of the sensor inside the patient's body using the detection of the non-physiological parameter or the detection of a predetermined level of the non-physiological parameter. Such a configuration may be beneficial when performing physiological measurements (such as, for example, pressure, temperature, blood flow, blood chemical analysis or the like) because the exact position of the sensor may be determined from the non-physiological parameter while the physiological measurement is performed. In the example of the optical signal application, a sensor that is light sensitive would be used in which, when a light is shown on it (for example, in an area just below the skin or through the skin), the sensor would be activated to indicate the position of the sensor element relative to the light. The detection of the magnetic field, X-ray field, electromagnetic field, and the like may operate similarly. If both physiological and non-physiological parameters are used, FIG. 8 shows a suitable configuration would include a sensor wire 401 comprising a first sensor element 408A and a second sensor element 408B disposed within the insertable portion at the distal end of the sensor wire 401. The other components of FIG. 8 have already been described in relation to FIG. 1.

Alternatively, the two sensor elements of FIG. 8 may measure two different physiological parameters or measure two different non-physiological parameters. Of course, any number of sensor elements may be used such as one, two, three, four, five, or more sensor elements in which the sensor elements may measure blood pressure; blood temperature; blood flow; one or more blood analyte concentrations; a magnetic field; a magnetic flux; an X-ray field; an electromagnetic field; an optical signal; the presence of a metallic instrument, implantable device, or a foreign object (such as, for example, a stent, needle, implantable drug delivery device, pacemaker, etc.), and/or any combination thereof.

Depending on the number of sensor elements, the transceiver unit of FIG. 4 then would have a corresponding number of sensor signal adapting circuitry. The sensor signal of each sensor element is then applied to its corresponding adapting circuitry to automatically generate an output signal, related to the sensor signal, in a format such that the measured variable is retrievable by the external device. One or more of the sensor signal adapting circuitries may comprise a programmable sensor conditioner or sensor conditioning means, a calibrator or calibrating means (being a storage device or means into which calibration data may be supplied, stored and altered, e.g. an electrically erasable programmable read-only memory (EEPROM)), an energy device or means and an output amplifier or output amplifying means.

The output signals from the sensor signal adapting circuitries may be communicated to the communication unit through the pair of communication modules, as described above. Of course, it also is contemplated that multiple pairs of communication modules may be used, such as, for example, one pair of communication modules for each type of sensor element.

Figure 9:
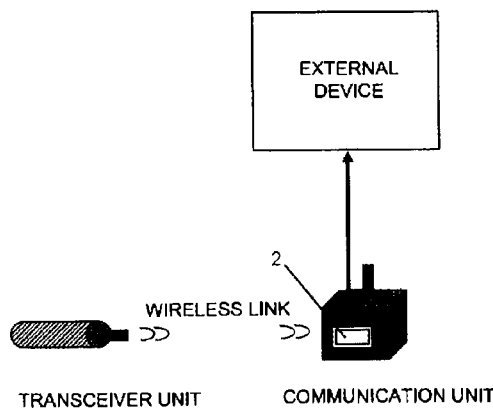
FIG. 9 schematically illustrates a transceiver, a communication unit, and an external device according to an embodiment of the present invention.
Figure 10:
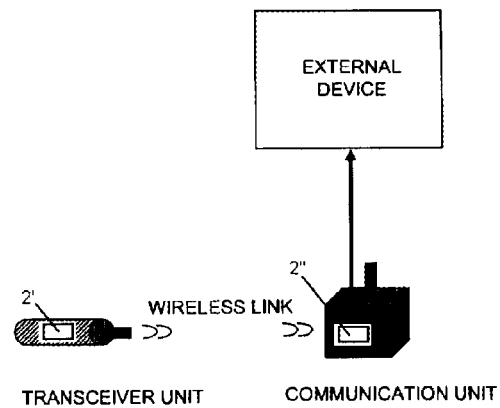
FIG. 10 schematically illustrates a transceiver, a communication unit, and an external device according to an embodiment of the present invention.
Figure 11:
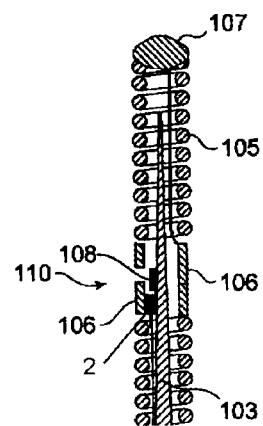
FIG. 11 schematically illustrates a measurement system according to an embodiment of the present invention.
Figure 12:
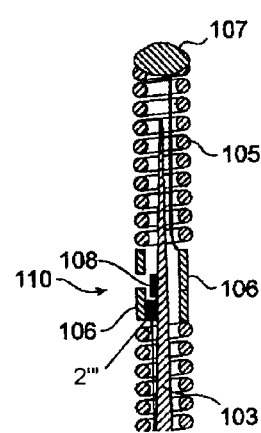
FIG. 12 schematically illustrates a measurement system according to an embodiment of the present invention.
Figure 13:
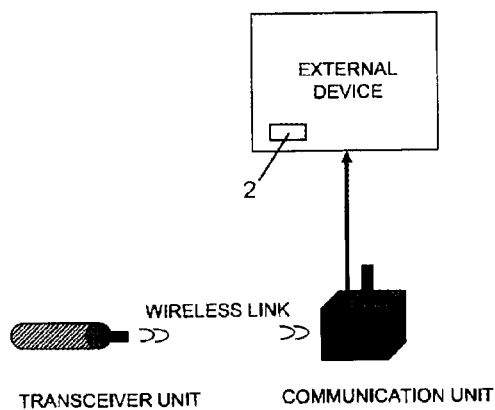
FIG. 13 schematically illustrates a transceiver, a communication unit, and an external device according to an embodiment of the present invention.
Figure 14:
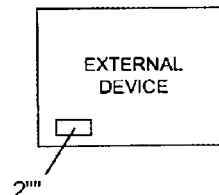
FIG. 14 schematically illustrates an external device according to an embodiment of the present invention.

Other embodiments are also contemplated for use of the sensor wire with one, two, three, four or more sensors. For example, the sensor signal adapting circuitry 2 is configured to filter, process, and format signal(s) received from the sensor wire. The sensor signal adapting circuitry 2 may be fully located within the housing of the transceiver unit (see FIG. 3) or fully located within the communication unit (see FIG. 9). The sensor signal adapting circuitry 2 may be partially located within the housing (a part of the circuitry is identified as 2' in FIG. 10) and be partially located within the communication unit (another part of the circuitry is identified as 2" in FIG. 10). The sensor signal adapting circuitry 2 may be fully located near the sensor(s) at the distal end of the sensor wire (see FIG. 11). The sensor signal adapting circuitry may be partially located near the sensor(s) at the distal end of the sensor wire (a part of the circuitry is identified as 2''' in FIG. 12) with the other portions of the sensor signal adapting circuitry being partially located within the housing and/or located within the communication unit. The sensor signal adapting circuitry 2 may be fully located at the external device (see FIG. 13). The sensor signal adapting circuitry may be partially located at the external device (a part of the circuitry is identified as 2'''' in FIG. 14) with the other portions of the sensor signal adapting circuitry being partially located within the housing, located within the communication unit, and/or near the sensor at the distal end of the sensor wire. When the sensor signal adapting circuitry is partially located within the housing, within communication unit, near the sensor(s) within the sensor wire, or within the external unit, the part of the circuitry may be the majority, a substantial portion, or a fraction of the sensor signal adapting circuitry needed to process the one or more sensors. For example, parts of the sensor signal adapting circuitry may be the programmable sensor conditioning means, the calibration means, the energy means, the output amplifying means, or subcomponents thereof in any combination for each sensor, a plurality of sensors, or for all the sensors.

Figure 15:
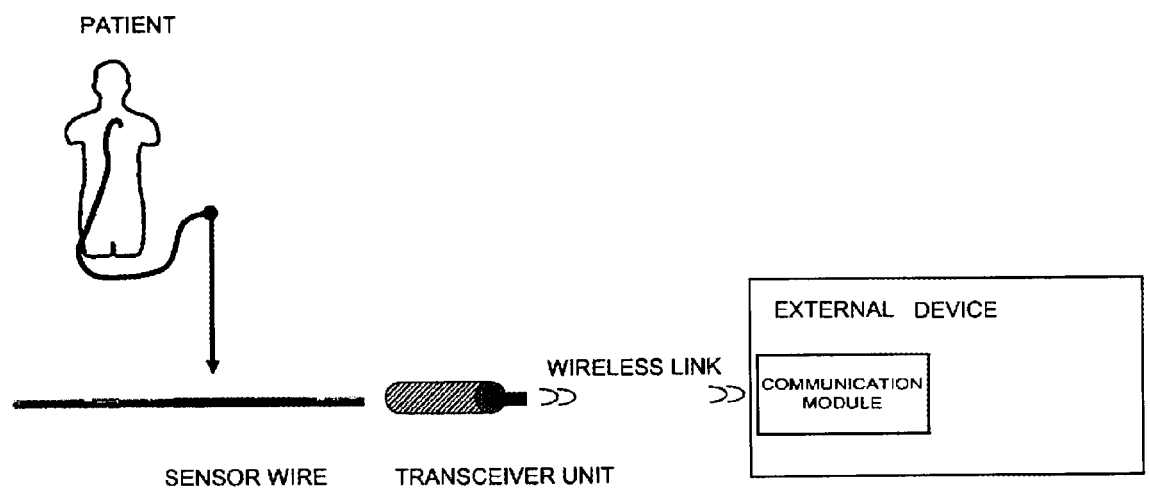
FIG. 15 schematically illustrates a measurement system according to an embodiment of the present invention.

Further embodiments are also contemplated. For example, FIG. 15 shows an embodiment in which the transceiver unit has a communication module that directly communicates with a communication module housed within the external device such that the communication unit of FIG. 2 is not needed. The external device therefore can have a communication module and/or have the sensor signal adapting circuitry partially or fully housed within the external device. As previously discussed, the external device may be a dedicated device (for example, a patient monitoring device, preferably provided with a monitor, or a PC (personal computer) provided with relevant software and external connections to receive and to process the measured data from the measurement system); a standard cath lab monitor system; a mobile unit (such as, for example, a mobile phone, an iPhone, or a Blackberry with specific applications) or a device where the data is sent directly to a mobile unit.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A blood pressure measurement system comprising:
 a pressure sensor guide wire comprising a pressure sensor located in a distal region of the pressure sensor guide wire that is configured to be inserted into a blood vessel of a human body;
 a transceiver unit communicatively coupled to the pressure sensor guide wire, the transceiver unit comprising:
  a housing adapted to be used external to the human body,
  a sensor signal adapting circuitry configured to process pressure sensor values generated by the pressure sensor to create processed pressure sensor values, and
  a first transceiver configured to wirelessly transmit a signal representing the processed pressure sensor values by performing steps comprising:
   wirelessly transmitting, at a first frequency, a first packet that includes at least a first processed pressure sensor value, a second processed pressure sensor value, and a third processed pressure sensor value, among the processed pressure sensor values,
   wirelessly transmitting, at a second frequency that is different from the first frequency, a second packet that includes at least the second processed pressure sensor value, the third processed pressure sensor value, and a fourth processed pressure sensor value, among the processed pressure sensor values, and
   wirelessly transmitting, at a third frequency that is different from the first and second frequencies, a third packet that includes at least the third processed pressure sensor value, the fourth processed pressure sensor value, and a fifth processed pressure sensor value, among the processed pressure sensor values.

2. The blood pressure measurement system according to claim 1, wherein the first transceiver is configured to wirelessly transmit the signal representing the processed pressure sensor values by performing steps further comprising wirelessly transmitting, at the first frequency, a fourth packet that includes at least the fourth processed pressure sensor value, the fifth processed pressure sensor value, and a sixth processed pressure sensor value, among the processed pressure sensor values.

3. The blood pressure measurement system according to claim 1, further comprising a second transceiver configured to wirelessly receive the signal representing the processed pressure sensor values transmitted from the first transceiver, wherein the second transceiver is connected with a patient monitoring device or personal computer, which is configured to display a representation of the processed pressure sensor values.

4. The blood pressure measurement system according to claim 3, wherein the transceiver unit is configured to be activated by a remote signal generated by the second transceiver in response to a command from the patient monitoring device or personal computer.

5. The blood pressure measurement system according to claim 1, wherein the sensor signal adapting circuitry is further configured to calibrate the pressure sensor values generated by the pressure sensor.

6. The blood pressure measurement system according to claim 5, wherein the sensor signal adapting circuitry comprises a memory configured to store calibration data.

7. The blood pressure measurement system according to claim 6, wherein the memory comprises an electrically erasable programmable read-only memory (EEPROM).

8. The blood pressure measurement system according to claim 7, wherein the sensor signal adapting circuitry comprises a programmable sensor conditioner.

9. The blood pressure measurement system according to claim 8, wherein the sensor signal adapting circuitry comprises an output amplifier.

10. The blood pressure measurement system according to claim 7, wherein the sensor signal adapting circuitry comprises an output amplifier.

11. The blood pressure measurement system according to claim 1, wherein the sensor signal adapting circuitry comprises a programmable sensor conditioner.

12. The blood pressure measurement system according to claim 11, wherein the sensor signal adapting circuitry comprises an output amplifier.

13. The blood pressure measurement system according to claim 1, wherein the sensor signal adapting circuitry comprises an output amplifier.

14. The blood pressure measurement system according to claim 1, wherein:
the pressure sensor guide wire further comprises a male connector; and
the transceiver unit further comprises a female connector configured to receive the male connector of the pressure sensor guide wire.

15. The blood pressure measurement system according to claim 14, wherein the transceiver unit is configured to be activated when the male connector of the pressure sensor guide wire is inserted into the female connector of the transceiver unit.

16. The blood pressure measurement system according to claim 1, wherein:
the housing of the transceiver unit comprises an activation button; and
the transceiver unit is configured to be activated via the activation button.

17. The blood pressure measurement system according to claim 1, further comprising an additional sensor located in the distal region of the pressure sensor guide wire, the additional sensor being configured to measure a magnetic field, a magnetic flux, an X-ray field, an electromagnetic field, and/or an optical signal generated outside the human body.

18. The blood pressure measurement system according to claim 1, further comprising an additional sensor located in the distal region of the pressure sensor guide wire, the additional sensor being configured to measure a presence of at least one of an implantable device, a foreign device, and/or a metallic device inside the body.

19. The blood pressure measurement system according to claim 1, further comprising an additional sensor located in the distal region of the pressure sensor guide wire, the additional sensor being configured to measure a temperature, a blood flow, and/or an amount of a blood analyte.

20. A blood pressure measurement method comprising:
inserting a distal region of a pressure sensor guide wire into a blood vessel of a human body, the pressure sensor guide wire comprising a pressure sensor located in the distal region;
generating pressure sensor values using the pressure sensor;
receiving a signal representing the pressure sensor values at a transceiver unit located external to the human body and communicatively coupled to the pressure sensor guide wire;
processing the signal representing the pressure sensor values sensed by the pressure sensor to create processed pressure sensor values, using the transceiver unit;
wirelessly transmitting a signal representing the processed pressure sensor values using a first transceiver of the transceiver unit, which comprises:
wirelessly transmitting, at a first frequency, a first packet that includes at least a first processed pressure sensor value, a second processed pressure sensor value, and a third processed pressure sensor value, among the processed pressure sensor values,
wirelessly transmitting, at a second frequency that is different from the first frequency, a second packet that includes at least the second processed pressure sensor value, the third processed pressure sensor value, and a fourth processed pressure sensor value, among the processed pressure sensor values, and
wirelessly transmitting, at a third frequency that is different from the first and second frequencies, a third packet that includes at least the third processed pressure sensor value, the fourth processed pressure sensor value, and a fifth processed pressure sensor value, among the processed pressure sensor values.

* * * * *